(12) United States Patent
Wendland et al.

(10) Patent No.: US 10,953,160 B2
(45) Date of Patent: Mar. 23, 2021

(54) INJECTION DEVICE WITH SLIDABLE MEMBER FOR REMOVING A CAP WITH A NEEDLE SHIELD

(71) Applicant: Sanofi-Aventis Deutschland GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 266 days.

(21) Appl. No.: 15/778,502

(22) PCT Filed: Nov. 21, 2016

(86) PCT No.: PCT/EP2016/078272
§ 371 (c)(1),
(2) Date: May 23, 2018

(87) PCT Pub. No.: WO2017/089282
PCT Pub. Date: Jun. 1, 2017

(65) Prior Publication Data
US 2019/0009037 A1    Jan. 10, 2019

(30) Foreign Application Priority Data
Nov. 27, 2015  (EP) .................................... 15196706

(51) Int. Cl.
*A61M 5/32*   (2006.01)
(52) U.S. Cl.
CPC ........ *A61M 5/3204* (2013.01); *A61M 5/3213* (2013.01); *A61M 2005/3252* (2013.01)

(58) Field of Classification Search
CPC .............. A61M 5/3204; A61M 5/3213; A61M 2005/3252; A61M 5/3203; A61M 5/3245; A61M 2005/3215; A61M 5/3243
See application file for complete search history.

(56) References Cited

U.S. PATENT DOCUMENTS 4,950,252 A    8/1990 Luther et al.
5,997,513 A    12/1999 Smith et al.
(Continued)

FOREIGN PATENT DOCUMENTS

CN    101541361    9/2009
CN    101827622    9/2010
(Continued)

OTHER PUBLICATIONS

PCT International Preliminary Report on Patentability in International Appln. No. PCT/EP2016/078272, dated May 29, 2018, 8 pages.
(Continued)

*Primary Examiner* — Laura A Bouchelle
*Assistant Examiner* — Anh Bui
(74) *Attorney, Agent, or Firm* — Fish & Richardson P.C.

(57) ABSTRACT

The present disclosure relates to an injection device. The injection device comprises a cap and a body for holding a syringe that has a needle at one end. The cap is removably attached to the body and has a needle shield to receive the needle. The injection device further comprises an actuator that is slidable relative to the body in the longitudinal direction of the body to urge the needle shield away from the body.

16 Claims, 3 Drawing Sheets

(56) References Cited

U.S. PATENT DOCUMENTS

| | | | |
|---|---|---|---|
| 7,223,259 B2* | 5/2007 | Marshall | A61M 5/3129 604/192 |
| 2009/0182284 A1* | 7/2009 | Morgan | A61M 5/3202 604/198 |
| 2009/0270672 A1 | 10/2009 | Fago | |
| 2013/0204229 A1* | 8/2013 | Olson | A61M 5/315 604/506 |

FOREIGN PATENT DOCUMENTS

| | | |
|---|---|---|
| CN | 204106753 | 1/2015 |
| CN | 104324438 | 2/2015 |
| CN | 104684603 | 6/2015 |
| EP | 2926861 A1 | 10/2015 |
| JP | 2004-531316 | 10/2004 |
| JP | 2009-526241 | 7/2009 |
| JP | 2011-509133 | 3/2011 |
| JP | 2012-513269 | 6/2012 |
| JP | 2013-508032 | 3/2013 |
| WO | WO 96/30065 | 10/1996 |
| WO | WO 02/087670 | 11/2002 |
| WO | WO 2014/029621 | 2/2014 |
| WO | WO 2015/048791 | 4/2015 |

OTHER PUBLICATIONS

PCT International Search Report and Written Opinion in International Appln. No. PCT/EP2016/078272, dated Feb. 27, 2017, 11 pages.

\* cited by examiner

INJECTION DEVICE WITH SLIDABLE MEMBER FOR REMOVING A CAP WITH A NEEDLE SHIELD

CROSS REFERENCE TO RELATED APPLICATIONS

This application is a U.S. national stage application under 35 USC § 371 of International Application No. PCT/EP2016/078272, filed on Nov. 21, 2016, which claims priority to European Application No. 15196706.4, filed on Nov. 27, 2015, the entire contents of which are incorporated herein by reference.

TECHNICAL FIELD

The present disclosure relates to an injection device.

BACKGROUND

Injection devices, such as auto-injectors, are known in the art for dispensing a medicament to the injection site of a patient. Such injection devices typically comprise a body and a cap. A needle syringe is located in the body. The cap is removably attached to the body to shield the needle of the needle syringe. To dispense the medicament, the cap is first pulled away from the body to expose the needle. The needle is then inserted into the body of the patient at the injection site to dispense the medicament.

The cap is held onto the body with sufficient force to ensure that the cap is not accidentally removed from the body during transport and storage of the injection device. This ensures that the needle is kept sterile and prevents the sharp needle from causing injury.

SUMMARY

An injection device is provided, comprising: a body for holding a syringe that has a needle at one end; a cap that is removably attached to the body and has a needle shield to receive the needle; and, an actuator that is slidable relative to the body in the longitudinal direction of the body to urge the needle shield away from the body.

The sliding movement of the actuator relative to the body to urge the needle shield away from the body may be easier for a user to perform than pulling the needle shield away from the body, particularly if the user is elderly or infirm. Therefore, the slidable actuator may facilitate removal of the cap from the body. Sliding of the actuator relative to the body may also allow for a more controlled separation of the needle shield from the body in comparison to pulling the cap away from the body.

At least a part of the actuator extends out of the body when the actuator is slid relative to the body to urge the needle shield away from the body. The part of the actuator may be located against an injection site of a patient prior to medicament being dispensed thereto. The part of the actuator comprises a needle sleeve. The needle sleeve is moveable relative to the body between an extended position, to shield the needle when a syringe is held in the body, and a retracted position, wherein the needle extends axially past an end of the needle sleeve. The actuator is configured such that when the actuator is slid relative to the body to urge the needle shield away from the body the needle sleeve moves to the extended position.

In one embodiment, the actuator is slidable towards the distal end of the injection device to urge the needle shield away from the body.

The elongate member may be slidably received in the body. This may allow for the injection device to be compact such that it is easy to store and transport. The actuator may comprise an elongate member. The elongate member may be in the form of a sleeve or partial sleeve.

The injection device may comprise an aperture to provide access to the actuator. Therefore, a part of the actuator may be accessible through the aperture such that the user can exert a force on the part of the actuator to slide the actuator relative to the body to urge needle shield away from the body. The aperture may comprise an elongate slot. The elongate slot may extend in the longitudinal direction of the body.

The actuator may comprise a grip portion. Therefore, the user may exert a force on the grip portion to slide the actuator relative to the body. The grip portion may be slidable relative to the body to urge the needle shield away from the body. The grip portion may comprise a groove. Thus, the user may insert a finger or fingernail into the groove to slide the actuator relative to the body. In an alternative embodiment, the grip portion comprises a projection. The projection may extend into the aperture such that the projection is slidable within the aperture. Thus, the user may exert a force on the projection to slide the actuator relative to the body to urge the needle shield away from the body. In one embodiment, the projection extends out of the aperture such that the projection protrudes from a peripheral wall of the body. In one embodiment, the grip portion comprises a trigger button.

The aperture may be arranged to limit the range of sliding movement of the projection within the aperture. Thus, the range of sliding movement of the actuator relative to the body may be limited to prevent the actuator from being extended too far out of the body or separated from the body. In one such embodiment, the aperture comprises first and second ends that form first and second stops.

In one embodiment, the actuator is slidable relative to the body between a first position, wherein a first part of the actuator may be inspected through the aperture in the body, and a second position, wherein a second part of the actuator may be inspected through the aperture in the body, and wherein the first and second parts of the actuator have different properties. In one such embodiment, the first and second parts of the actuator have different visual properties such as different colours and/or different text that may be inspected through the aperture. This may allow the user to observe whether the needle shield has been urged away from the body.

The cap may include a shoulder and the actuator may be configured to be urged against the shoulder to urge the needle shield away from the body.

The cap may comprise a finger hole. Thus, a user may insert a finger into the finger hole to grip the cap to pull the cap away from the body with one hand whilst exerting a force on the actuator with the other hand to slide the actuator relative to the body such that removal of the cap from the body is facilitated.

In one embodiment, the injection device comprises an actuator lock that is movable between a locked state, wherein the actuator is held in position relative to the body in the longitudinal direction of the body, and an unlocked state, wherein the actuator is movable relative to the body in the longitudinal direction of the body.

The cap may comprise one or more flanged portions. The flanged portions may be configured to allow the user to grip the flanged portions. Thus, the user may grip the or each flanged portion with one hand to pull the cap away from the body whilst exerting a force on the actuator with the other hand to slide the actuator relative to the body such that removal of the cap from the body is facilitated.

The injection device may further comprise a syringe having a needle at one end and being received in the body, wherein the needle shield is in frictional engagement with the syringe when the cap is attached to the body. The friction may help to retain the needle shield on the syringe. The syringe may contain a medicament.

In one embodiment, the cap further comprises an outer cap. The needle shield may be received in the outer cap.

In one embodiment, the injection device is an auto-injector.

There is also provided a method of removing a cap from a body of an injection device, wherein the body holds a syringe that has a needle at one end and wherein the cap is removably attached to the body and has a needle shield to receive the needle, the method comprising: sliding an actuator relative to the body in the longitudinal direction of the body such that at least a part of the actuator extends out of the body to urge the needle shield away from the body, wherein the part of the actuator comprises a needle sleeve moveable relative to the body between an extended position, to shield the needle, and a retracted position, wherein the needle extends axially past an end of the needle sleeve, and wherein sliding the actuator relative to the body to urge the needle shield away from the body moves the needle sleeve to the extended position.

The pulling motion required to remove the cap from the body can make cap removal difficult for the patient, particularly if the patient is elderly or infirm. Some embodiments reduce the amount of force required to remove the cap from the body.

These and other aspects will be apparent from and elucidated with reference to the embodiments described hereinafter.

BRIEF DESCRIPTION OF THE FIGURES

Embodiments of the invention will now be described, by way of example only, with reference to the accompanying drawings, in which.

DETAILED DESCRIPTION

Figure 1A:
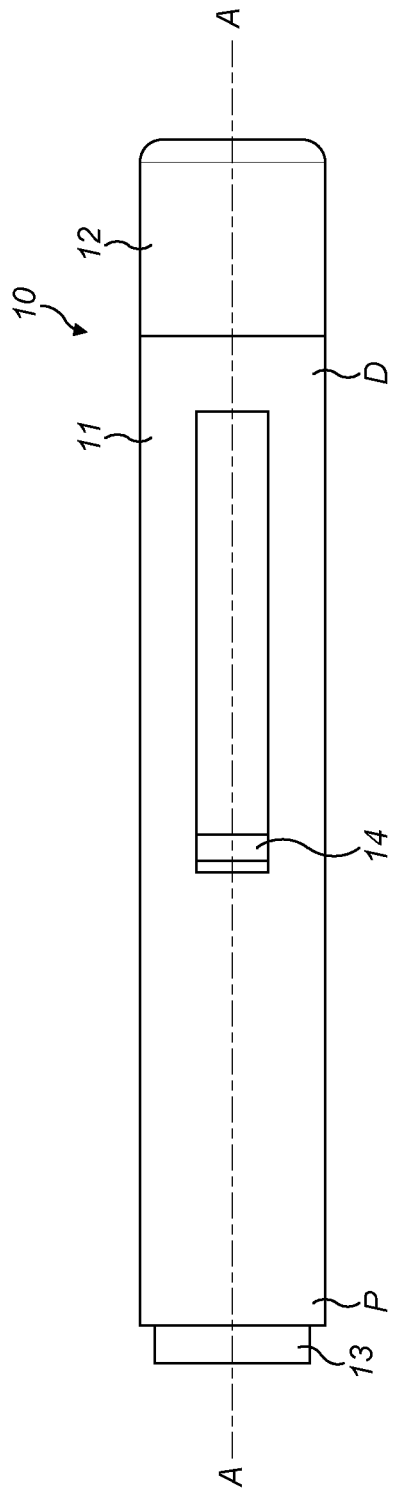
FIG. 1A is a schematic side view of an auto-injector, with a cap attached to a body of the auto-injector.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction, can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
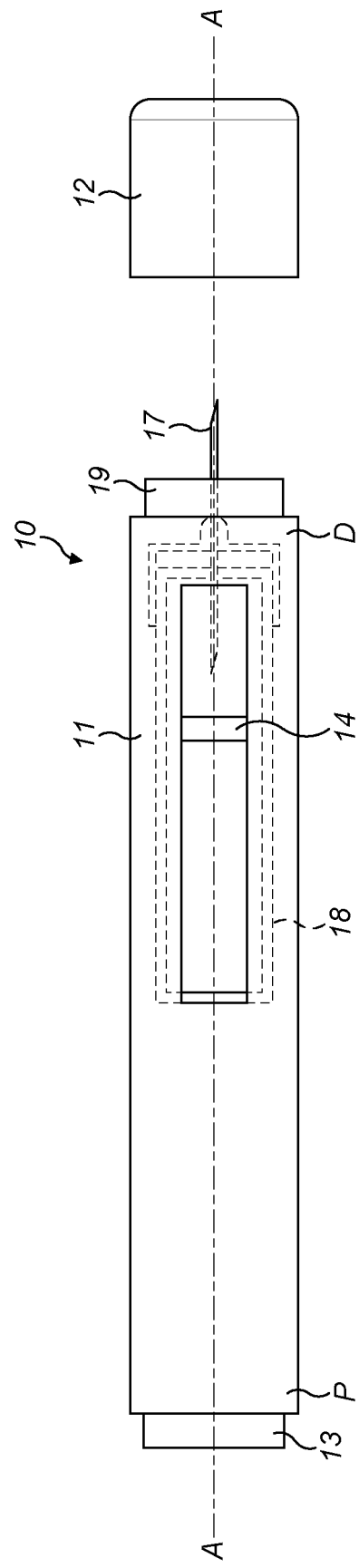
FIG. 1B is a schematic side view of the auto-injector of FIG. 1A, with the cap removed from the body.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated," whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 2:
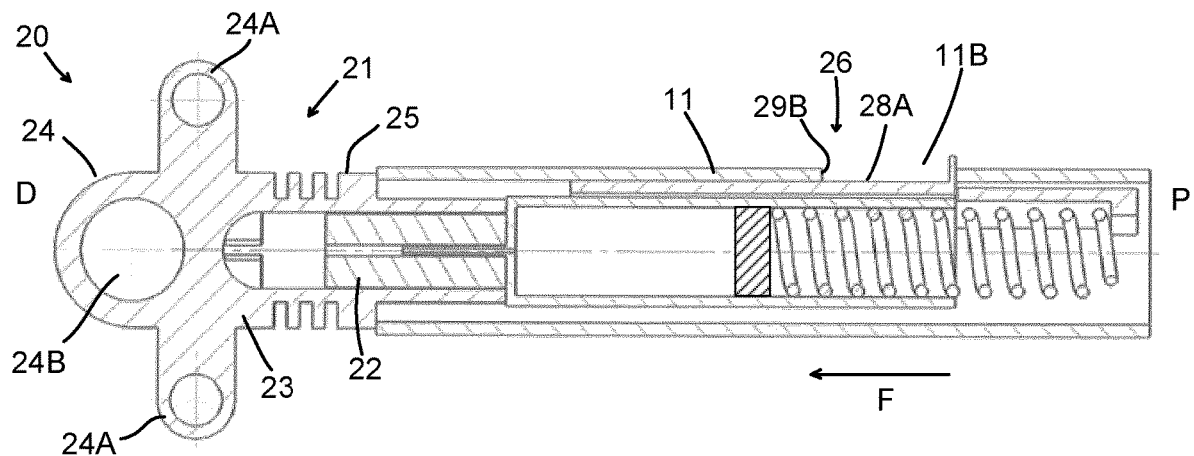
FIG. 2 is a schematic cross-sectional side view of an auto-injector according to a first embodiment, wherein a cap is attached to a body of the auto-injector.
Figure 3:
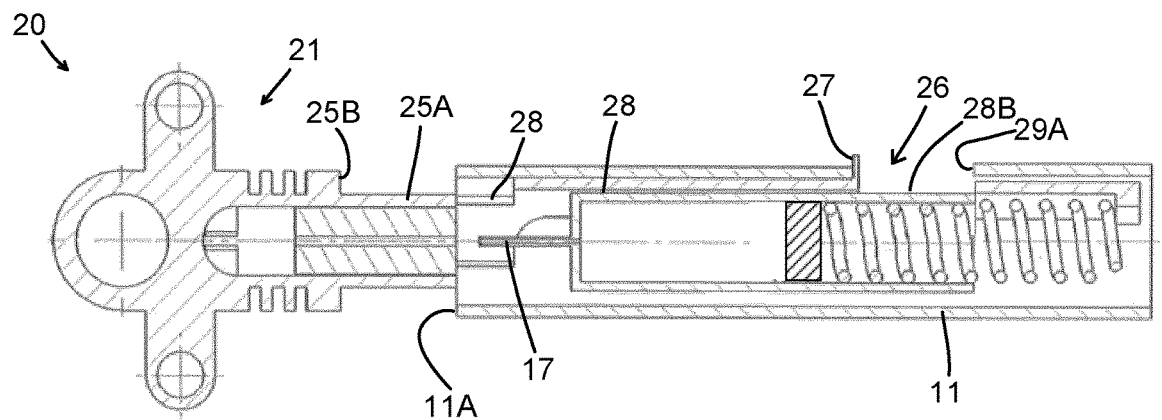
FIG. 3 is a schematic cross-sectional side view of the auto-injector of FIG. 2, wherein the cap is partially removed from the body; and, FIG. 4 is a schematic cross-sectional top view of the auto-injector of FIG. 2, wherein the cap is partially removed from the body.
Figure 4:
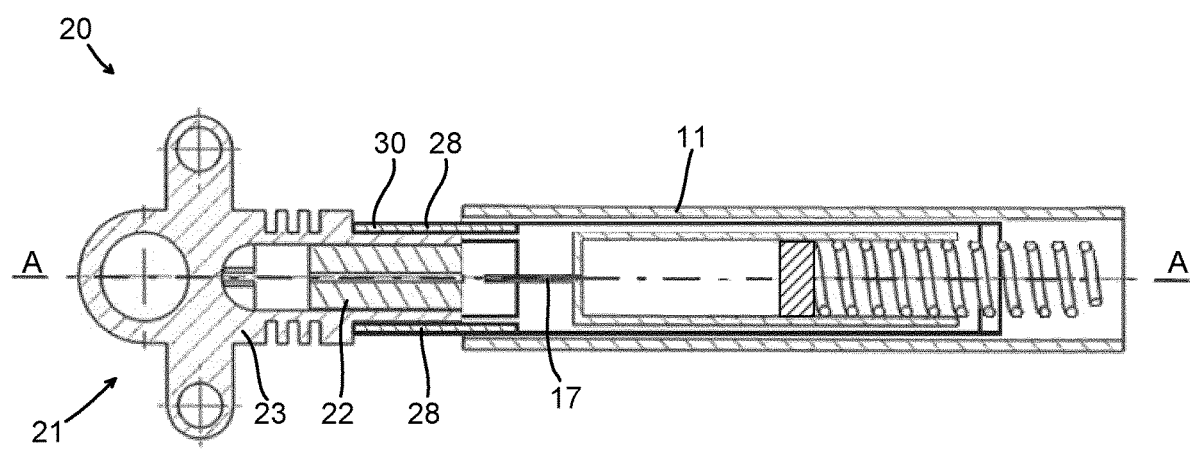

Referring now to FIGS. 2 to 4, an injection device 20 according to a first embodiment is shown. The injection device 20 is in the form of an auto-injector 20 that has similar features to the auto-injector 10 described above in relation to FIGS. 1A and 1B, with like features retaining the same reference numerals. A difference is that the cap 12 of the auto-injector 10 described above is omitted and is replaced with an alternative cap 21 and the auto-injector 20 further comprises an actuator 26.

The cap 21 of the auto-injector 20 of the first embodiment comprises a needle shield 22 and an outer cap 23. The needle shield 22 is received within the outer cap 23. The needle shield 22 is fixed relative to the outer cap 23. For example, the needle shield 22 and outer cap 23 may be attached in a force-fit, form-fit, or bonded connection. Alternatively, the needle shield 22 and outer cap 23 may be integrally formed.

The outer cap 23 comprises a finger grip portion 24 and a sleeve 25. The finger grip portion 24 comprises a finger hole 24A located towards the proximate end P of the auto-injector 20. The user may put a finger through the finger hole 24A to pull the outer cap 23 away from the body 11. In addition, the finger grip portion 24 comprises a plurality of flanged portions 24B that extend radially away from the central axis A-A of the auto-injector 20. The user may grip the flanged portions 24B to pull the outer cap 23 away from the body 11.

The sleeve 25 of the outer cap 23 extends from the finger grip portion 24 towards the proximal end P of the auto-injector 20 when the cap 21 is attached to the body 11. The sleeve 25 comprises a tubular end portion 25A, for receiving the needle shield 22, and a shoulder 25B. The tubular end portion 25A is configured to be received in the open distal end 11A of the body 11 such that the needle shield 22 receives the needle 17 to shield the needle 17 and a portion of the shoulder 25B abuts the open distal end 11A of the body 11.

In an exemplary embodiment (not shown), the shoulder 25B may comprise a lock to prevent unintentional removal of the cap 21 from the body 11. In one such embodiment, the lock comprises at least one recess (not shown) that corresponds with a locking protrusion (not shown) located at the open distal end 11A of the body 11. The locking protrusion engages with the recess to prevent the cap 21 from unintentionally being removed from the body 11. The actuator 26 is received in the body 11 of the auto-injector 20 and is slidable relative to the body 11 in the direction of the central axis A-A of the auto-injector 20. The body 11 comprises an aperture 11B in the peripheral wall of the body 11. The actuator 26 comprises a grip portion 27. The user may exert a force on the grip portion 27 to slide the actuator 26 relative to the body 11. In the present embodiment, the grip portion 27 is in the form of a projection 27 that extends out of the aperture 11B in the body 11.

The actuator 26 further comprises an elongate member 28 that may extend out of the open distal end 11A of the body 11 (as shown in FIG. 4) when the projection 27 is slid towards the open distal end 11A. The elongate member 28 is in the form of a partial sleeve that subtends partially around the central axis A-A of the auto-injector 20. The elongate member 28 extends inside the body 11 from the projection 27 to abut the shoulder 25B of the outer cap 23 when the cap 21 is attached to the body 11. In alternative embodiments (not shown), the elongate member is in the form of a sleeve/tubular element or one or more arms that are slidably received in the body. The elongate member 28 may be generally cylindrical.

The actuator 26 is configured such that linear movement of the projection 27 relative to the body 11 in the direction of the central axis A-A of the auto-injector 20 results in corresponding movement of the elongate member 28, which is fixed relative to the projection 27. The projection 27 and elongate member 28 are integrally formed. In an alternative embodiment (not shown), the projection is adhered to the elongate member.

When the actuator 26 is in a first position (shown in FIG. 2), the projection 27 is located near to the proximal end P of the auto-injector 20 such that the elongate member 28 of the actuator 26 is retracted into the open distal end 11A of the body 11.

The cap 21 is initially attached to the body 11 such that the needle 17 is received in the needle shield 22 (as shown in FIG. 2) and the actuator 26 is in the first position. Thus, the needle 17 is covered by the needle shield 22 to keep the needle 17 sterile, and to prevent the needle 17 from causing injury to the patient. Furthermore, the elongate member 28 abuts the shoulder 25B of the outer cap 23. In one embodiment, the elongate member 28 is engaged with the shoulder 25B by a force-fit or form-fit connection that may be released in an easy manner.

To inject medicament, the cap 21 is first removed from the body 11. Removal of the cap 21 from the body 11 is achieved by the patient exerting a force on the projection 27 of the actuator 26 to urge the projection 27 relative to the body 11 towards the distal end D of the auto-injector 20 (in the direction of arrow 'F' in FIG. 2). This causes the elongate member 28 to be urged against the cap 21 such that the elongate member 28 and the cap 21 are urged out of the open distal end 11A of the body 11. More specifically, the elongate member 28 moves linearly in the same direction as the projection 27 such that the elongate member 28 is urged against the shoulder 25B of the outer cap 23 to exert a force on the outer cap 23 that urges the outer cap 23 out of the open distal end 11A of the body 11. Therefore, the needle shield 22, which is fixed relative to the outer cap 23, is urged out of the open distal end 11A of the body 11 such that the needle shield 22 moves away from the needle 17. However, it should be recognised that in alternative embodiments (not shown), the elongate member 28 is instead urged against another part of the cap 21, for example the needle shield 22 or the tubular end portion 25A of the sleeve 25, to move the cap 21 away from the open distal end 11A of the body 11.

The patient continues to exert a force on the projection 27 until the actuator 26 reaches a second position (as shown in FIGS. 3 and 4), wherein the projection 27 is located closer to the distal end D of the auto-injector 20 than in the first position and the needle shield 22 is separated from the needle 17. When the actuator 26 is in the second position, the cap 21 is removed from the body 11 and the tubular portion 25A of the outer cap 23 is received on the elongate member 28. Thus, the cap 21 may easily be removed to provide access to the needle 17 simply by pulling the outer cap 23 away from the elongate member 28. The friction between the cap 21 and the elongate member 28 when the actuator is in the second position may be less than the friction between the cap 21 and the body 11 and needle 17 when the actuator is in the first position. In such an embodiment, less force is required to remove the cap 21 from the elongate member 28 when the actuator 26 is in the second position than to remove the cap 21 from the body 11 when the actuator 26 is in the first position.

Optionally, the cap 21 may be retained on the elongate member 28 by a clip (not shown). Thus, after the needle shield 22 is separated from the needle 17, the user is able to unclip the cap 21 from the elongate member 28 to provide access to the needle 17.

With the cap 21 removed from the body 11 and elongate member 28, the elongate member 28 is pressed up against an injection site of the patient. The dispense button 13 is then pressed to cause the dispense mechanism (not shown) to move the needle 17 towards the injection site and to dispense medicament to the injection site. In an alternative embodiment (not shown), the dispense mechanism is configured such that the movement of the needle towards the injection site and/or the dispensing of the medicament occurs automatically when the elongate member is pressed against the injection site. In yet another embodiment, after the cap has been removed from the elongate member, the user then slides the actuator back to the first position such that the elongate member is retracted back into the open distal end of the body. The open distal end of the body is then pressed up against the injection site of the patient and the needle is then moved towards the injection site to dispense medicament thereto.

The part of the elongate member 28 that extends out of the open distal end 11A of the body 11 when the projection 27 is slid to move the actuator 26 towards the second position comprises a needle sleeve 30. The needle sleeve 30 is moveable relative to the body 11 between an extended position, to shield the needle 17, and a retracted position, wherein the needle 17 extends axially past the end of the needle sleeve 30. The needle 17 may extend past the open distal end 11A of the body 11 when the cap 21 is removed from the body 11. To inject medicament, the distal end of the needle sleeve 30 is pressed up against an injection site of the patient, which causes the needle sleeve 30 to move from the extended position to the retracted position such that the needle 17 enters the injection site. In one embodiment, the needle sleeve 30 extends fully about the longitudinal axis of the needle 17 when the needle sleeve 30 is in the extended position. In an alternative embodiment, the needle sleeve 30 extends partially about the longitudinal axis of the needle 17 when the needle sleeve 30 is in the extended position.

The sliding movement of the projection 27 relative to the body 11 to remove the cap 21 from the body 11 may be easier for the user to perform in comparison to injection devices that require the cap to be manually pulled away from the body, particularly if the user is elderly or infirm. In addition, the actuator 26 may allow for a smooth and controlled separation of the needle shield 22 from the needle 17.

The actuator 26 may comprise an indicator that may be inspected through the aperture 11B in the body 11 when the actuator 26 is in the first position to indicate to the patient that the needle shield 22 is covering the needle 17 and must be removed prior to injection. In one embodiment, a first part 28A of the elongate member 28 is visible through the aperture 11B when the actuator 26 is in the first position and a second part 28B of the elongate member 28 is visible through the aperture 11B when the actuator 26 is in the second position. The first and second parts 28A, 28B of the elongate member 28 have different properties, for example being visibly different or have a different texture. For instance, the first and second parts 28A, 28B of the elongate member 28 may be different colours, have different symbols or drawings imprinted thereon, or may comprise different text or Braille. Depending on the position of the actuator 26, one of the first or second parts 28A, 28B of the elongate member 28 is visible and/or may be inspected through the aperture 11B in the body 11.

In an exemplary embodiment (not shown), the injection device 20 comprises an actuator lock (not shown) that is configured to prevent unintentional movement of the actuator 26 relative to the body 11. In one such embodiment (not shown), the actuator lock is moveable from a locked state, wherein the actuator 26 is held in the first position relative to the body 11, to an unlocked state, wherein the actuator 26 is moveable from the first positon to the second position to remove the cap 21 from the body 11. The actuator lock may comprise a locking member (not shown) that engages with the actuator 26. The locking member may comprise, for example, a latch or movable pin that engages with the actuator 26 to hold the actuator 26 in position relative to the body 11. In one embodiment, the actuator lock comprises an electronically actuated latch for holding the actuator 26 in position relative to the body 11.

The aperture 11B is in the form of a slot 11B in the body 11. The length of the slot 11B in the direction of the central axis A-A of the auto-injector 20 may limit the range of movement of the projection 27 relative to the body 11. This is because the slot 11B comprises first and second ends 29A, 29B which form first and second stops 29A, 29B. When the projection 27 is in the first position it abuts the first end 29A of the slot 11B and when the projection 27 is in the second position it abuts the second end 29B of the slot 11B.

To remove the cap 21 from the body 11, the user may additionally pull the cap 21 from the body 11. For example, the user may insert a finger into the finger hole 24A of the finger grip portion 24 and/or may grip the flanged portions 24B of the finger grip portion 24 to pull the outer cap 23 away from the open distal end 11A of the body 11. This may be performed at the same time as, or after, the projection 27 is slid towards the open distal end 11A of the body 11.

In the above described embodiment, the elongate member 28 extends out of the open distal end 11A of the body 11 when the actuator 26 is slid towards the distal end D of the auto-injector 20. Thus, the elongate member 28 is pressed against the injection site of the patient. However, in an alternative embodiment (not shown), the elongate member is urged towards the open distal end of the body when the projection is slid towards the open distal end of the body but does not extend out of the open distal end. For example, the elongate member may instead be urged against the tubular end portion of the sleeve, instead of the shoulder of the sleeve, when the projection is slid towards the open distal end of the body. In such alternative embodiments, the open distal end of the body is pressed against the injection site prior to the medicament being dispensed.

In the above described embodiments, the needle is moved relative to the body by a dispensing mechanism such that the needle is moved towards the injection site. However, in alternative embodiments (not shown) the needle remains stationary relative to the body. In one alternative embodiment (not shown), the elongate member is retractable into the open distal end of the body when the needle shield has been removed and the open distal end of the body is pressed against the injection site. The needle projects from the open distal end of the body and therefore penetrates the injection site.

In the above described embodiment, the needle shield 22 is separated from the needle 17 but the cap 21 is still retained on the elongate member 28 when the actuator 26 is moved from the first position to the second position. The cap 21 is then removed from the elongate member 28 by the user. However, in an alternative embodiment (not shown), the actuator is configured such that the cap is completely removed from the body and elongate member when the actuator is moved from the first position to the second position. In one such embodiment, the elongate member is urged against the needle shield and/or the tubular end portion of the sleeve of the outer cap when the actuator is moved from the first position to the second position. The needle shield may be fixedly secured to the outer cap such that if one of the needle shield and outer cap is urged away from the body by the elongate member, the other one of the needle shield and outer cap is also urged away from the body.

In the above described embodiment, the needle shield 22 is fixed relative to the outer cap 23. However, in an alternative embodiment (not shown) the needle shield 22 is moveable relative to the outer cap 23 in the direction of the central axis A-A. For example, the needle shield 22 may be slidably received in the outer cap 23. In one such embodiment, the elongate member 28 is urged against the needle shield 22 when the actuator 26 is moved from the first positon to the second position such that the needle shield 22 is slid relative to the end cap 23 and moves away from the needle 17. The cap 21 is then removed from the body 11 by the patient.

Although in the above described embodiment the auto-injector 20 comprises one projection 27, in alternative embodiments (not shown) the auto-injector comprises a plurality projections and the user may slide one or more of the projections relative to the body to remove the cap from the body. In one such embodiment, the auto-injector comprises a plurality of apertures in the body and each projection is slidably received in a respective aperture. Each projection may extend from a single elongate member. Alternatively, the auto-injector may comprise a plurality of elongate members and each projection may extend from a corresponding elongate member.

In the above described embodiment, the grip portion 27 is in the form of a projection 27. However, in alternative embodiments (not shown) the grip portion is instead in the form of a groove or recess in the elongate member. The groove or recess is accessible through the aperture in the body. Thus, the user may insert a finger or fingernail into the groove or recess to exert a force on the elongate member to slide the actuator relative to the body such that the needle shield is urged away from the body.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides.

Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance, which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na$^+$, or K$^+$, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. An injection device comprising:
a body for holding a syringe that has a needle at one end;
a cap that is removably attached to the body and has a needle shield received within the cap to receive the needle; and
an actuator that is slidable relative to the body in a longitudinal direction of the body to urge the needle shield away from the body,
wherein at least a part of the actuator extends out of the body when the actuator is slid relative to the body to urge the needle shield away from the body, and wherein the part of the actuator which extends out of the body to urge the needle shield away from the body comprises a needle sleeve moveable relative to the body between an extended position, to shield the needle when the syringe is held in the body, and a retracted position, wherein in the extended position, an end of the needle sleeve extends axially past the needle, and in the retracted position, the needle extends axially past the end of the needle sleeve, and
wherein the actuator is configured such that when the actuator is slid relative to the body to urge the needle shield away from the body, the needle sleeve moves to the extended position.

2. The injection device according to claim 1, wherein the injection device comprises an actuator lock that is movable between a locked state, wherein the actuator is held in position relative to the body in the longitudinal direction of the body, and an unlocked state, wherein the actuator is movable relative to the body in the longitudinal direction of the body.

3. The injection device according to claim 1, wherein the actuator comprises a grip portion.

4. The injection device according to claim 3, wherein the body comprises an aperture to provide access to the grip portion.

5. The injection device according to claim 4, wherein the grip portion comprises a projection that extends into the aperture such that the projection is slidable within the aperture.

6. The injection device according to claim 5, wherein the aperture is arranged to limit a range of sliding movement of the projection within the aperture.

7. The injection device according to claim 4, wherein the actuator is slidable relative to the body between a first position, wherein a first part of the actuator may be inspected through the aperture in the body, and a second position, wherein a second part of the actuator may be inspected through the aperture in the body, and wherein the first and second parts of the actuator have different properties.

8. The injection device according to claim 1, wherein the cap includes a shoulder and wherein the actuator is configured to be urged against the shoulder to urge the needle shield away from the body.

9. The injection device according to claim 1, wherein the cap comprises a finger hole or at least one flanged portion configured to be gripped by a user to facilitate the cap being pulled away from the body.

10. The injection device according to claim 1, comprising the syringe received in the body, wherein the needle shield is in frictional engagement with the syringe when the cap is attached to the body.

11. The injection device according to claim 10, wherein the syringe contains a medicament.

12. The injection device according to claim 1, wherein the injection device is an auto-injector.

13. A method of removing a cap from a body of an injection device, wherein the body holds a syringe that has a needle at one end and wherein the cap is removably attached to the body and has a needle shield received within the cap to receive the needle, the method comprising:

sliding an actuator relative to the body, in a longitudinal direction of the body, such that at least a part of the actuator extends out of the body, to urge the needle shield away from the body, wherein the part of the actuator which extends out of the body to urge the needle shield away from the body comprises a needle sleeve moveable relative to the body between an extended position, to shield the needle, and a retracted position, wherein in the extended position, an end of the needle sleeve extends axially past the needle, and in the retracted position, the needle extends axially past the end of the needle sleeve, and wherein sliding the actuator relative to the body to urge the needle shield away from the body moves the needle sleeve to the extended position.

14. The method of claim 13 further comprising moving the actuator into a locked position, wherein the actuator is held in position relative to the body in the longitudinal direction of the body.

15. The method of claim 14, wherein the actuator comprises a movable lock.

16. The method of claim 13 further comprising moving the actuator of the injection device into an unlocked position, wherein in the unlocked position, the actuator is movable relative to the body in the longitudinal direction of the body.

* * * * *